United States Patent [19]

Bennett et al.

[11] Patent Number: 5,168,064
[45] Date of Patent: Dec. 1, 1992

[54] ENDO-1,4-BETA-GLUCANASE GENE AND ITS USE IN PLANTS

[75] Inventors: Alan B. Bennett, Davis; Robert L. Fischer, El Cerrito; Coralie Lashbrook, Dixon; James Giovannoni, San Francisco, all of Calif.

[73] Assignee: The Regents of the University of California, Oakland, Calif.

[21] Appl. No.: 511,417

[22] Filed: Apr. 20, 1990

[51] Int. Cl.$^5$ .................. C12N 15/00; C12N 5/00; C12N 9/42; C12P 21/04; C07H 15/12

[52] U.S. Cl. .................. 435/320.1; 435/69.1; 435/69.8; 435/70.1; 435/172.3; 435/209; 435/240.4; 935/48; 935/67; 536/27

[58] Field of Search ............ 435/69.1, 69.7, 69.8, 435/70.1, 172.3, 240.4, 320.1, 209; 536/27; 935/47, 48, 67

[56] References Cited

U.S. PATENT DOCUMENTS 4,801,540 1/1989 Hiatt et al. ................. 435/172.3

FOREIGN PATENT DOCUMENTS 0240208 10/1987 European Pat. Off. .
0271988 6/1988 European Pat. Off. .

OTHER PUBLICATIONS

Tigchelaar, E. C., et al., "Genetic Regulation of Tomato Fruit Ripening," *Hortic. Sci.*, 13:508–513 (1978).
Smith, C. J. S., et al., "Antisense RNA inhibition of polygalacturonase gene expression in transgenic tomatoes," *Nature*, 334:724–726 (1988).
Sheehy, R. E., et al., "Reduction of polygalacturonase activity in tomato fruit by antisense RNA," *Proc. Nat. Acad. Sci.*, 85:8805–8809 (1988).
Smith, C. J. S., et al., "Inheritance and effect on ripening of antisense polygalacturonase genes in transgenic tomatoes," *Plant Molecular Biology*, 14:369–379, (1990).
Hatfield, R., and Nevins, D. J., "Characterization of the Hydrolytic Activity of Avocado Cellulase," *Plant Cell Physiol.*, 27(3):541–552 (1986).
Christoffersen, R. E., et al., "Cellulase gene expression in ripening avocado fruit: The accumulation of cellulase mRNA and protein as demonstrated by cDNA hybridization and immunodetection," *Plant Molecular Biol.*, 3:385–391 (1984).
Tucker, M. L., et al., "Bean Abscission Cellulase," *Plant Physiol.*, 88:1257–1262 (1988).
Sobotka et al., 1971, J. Amer. Soc. Hort. Sci. 96(6):705–707.
Bennett et al., 1986, Plant Physio. 81:830–835.
Sobotka et al., 1974 Plant Physiology 53:759–763.

*Primary Examiner*—David T. Fox
*Attorney, Agent, or Firm*—Townsend and Townsend

[57] ABSTRACT

The present invention provides a method for reducing fruit softening and cell wall polysaccharide degradation by inhibiting endo-1,4-β-glucanase activity using antisense DNA constructions.

2 Claims, 1 Drawing Sheet

ENDO-1,4-BETA-GLUCANASE GENE AND ITS USE IN PLANTS

This invention was made with Government support under Grant Nos. CRCR-87-1-2525 and CRCR-87-1-2526 awarded by the U.S. Department of Agriculture. The Government has certain rights in this invention.

BACKGROUND OF THE INVENTION

1. Field of the Invention

The present invention relates generally to methods for reducing fruit softening. In particular, it relates to methods for reducing fruit softening and cell wall polysaccharide degradation by inhibiting the activity of endo-1,4-β-glucanase.

2. Information Disclosure

Ripening, the final phase of fruit development, involves a number of dramatic metabolic changes in fruit tissue. An important aspect of the ripening process is fruit softening, which is thought to result primarily from modifications of the cell wall. Many subtle changes in metabolic activity are involved in this response.

The prior art discloses ripening-impaired mutants, such as the rin mutant which have been used to study fruit ripening. Tigchelaar *Hortic. Sci.*, 13:508-513, 1978. The use of these mutants to specifically control fruit softening has met with limited success, however, because of the pleiotropic nature of these mutations.

An increase in the activity of polygalacturonase, an enzyme responsible for the degradation of pectin, has been correlated with fruit softening. Recombinant constructs have been prepared containing a plant promoter linked to polygalacturonase cDNA in the antisense direction. These constructs have been inserted into tomato to inhibit the activity of this enzyme in ripening fruit. Smith et al., *Nature,* 334:724-726, 1988; Sheehy et al., *Proc. Nat. Acad. Sci.,* 85:8805-8809, 1988; Hiatt et al., U.S. Pat. No. 4,801,340; Bridges et al., EPO Publication No. 0,271,988. Although these constructs have been shown to inhibit polygalacturonase activity, an effect on fruit softening has not been shown. Smith et al., *Plant Mol.* 14:369-379, 1990.

Endo-1,4-β-glucanase is another enzyme thought to be involved in fruit softening. It is known to degrade the major hemicellulosic polymer, xyloglucan. Hatfield and Nevins, *Plant and Cell Physiol.,* 27:541-552, 1986. The cDNA and gene encoding endo-1,4-β-glucanase have been cloned from avocado (Christoffersen et al., *Plant Molec. Biol.,* 3:385, 1984) and bean (Tucker et al., *Plant Physiol.,* 88:1257, 1988).

SUMMARY OF THE INVENTION

The present invention relates to a method of reducing fruit softening and inhibiting the degradation of cell wall polymers comprising, introducing into a plant an expression cassette having a plant promoter sequence operably linked to a DNA subsequence of at least 20 base pairs derived from a DNA sequence encoding endo-1,4-β-glucanase, the DNA subsequence being linked to the promoter sequence in the opposite orientation for expression. The promoter can be either inducible or constitutive. If inducible, it is preferably derived from the tomato E8 gene. If constitutive, it is preferably the 35S promoter of cauliflower mosaic virus.

The method can be modified by introducing into a plant an expression cassette as described above plus an expression cassette having a plant promoter sequence operably linked to a DNA subsequence of at least 20 base pairs derived from a DNA sequence encoding polygalacturonase, the DNA subsequence being linked to the promoter sequence in the opposite orientation for expression.

The preferred plant for the method is tomato. The expression cassette can be introduced into the plant by any in vitro technique, preferably using Agrobacterium. The expression cassette can also be introduced into the plant by a sexual cross.

The present invention also provides a method of inhibiting endo-1,4-β-glucanase activity comprising, introducing into a plant an expression cassette having a plant promoter sequence operably linked to a DNA subsequence of at least 20 base pairs derived from a DNA sequence encoding endo-1,4-β-glucanase, the DNA subsequence being linked to the promoter sequence in the opposite orientation for expression. By inhibiting the enzyme, cell wall polysaccharide degradation can be inhibited. The preferred embodiments as described above apply to this method, as well, except that an expression cassette comprising polygalacturonase antisense DNA is not used.

The present invention further provides an expression cassette comprising a plant promoter sequence operably linked to a DNA subsequence of at least 20 base pairs derived from a DNA sequence encoding endo-1,4-β-glucanase, the DNA subsequence being linked to the promoter sequence in the opposite orientation for expression. The promoter can be inducible, typically the E8 promoter, or constitutive, typically derived from cauliflower mosaic virus.

A plant, preferably tomato, is also provided that contains an expression cassette having a plant promoter sequence operably linked to a DNA subsequence of at least 20 base pairs derived from a DNA sequence encoding endo-1,4-β-glucanase, the DNA subsequence being linked to the promoter sequence in the opposite orientation for expression.

The present invention further provides a DNA sequence which is uninterrupted, which encodes endo-1,4-β-glucanase, and which is flanked on at least one side by non-wild type DNA. The DNA sequence is typically a cDNA sequence derived from tomato.

Further, an expression cassette is provided which comprises a promoter sequence operably linked to a DNA sequence which is uninterrupted and which encodes endo-1,4-β-glucanase. The DNA sequence is typically a cDNA sequence derived from tomato. The promoter sequence function in both prokaryotes and eukaryotes.

The present invention also provides a method of isolating from a plant a DNA sequence encoding endo-1,4-β-glucanase comprising, probing a DNA library prepared from plant tissue with oligonucleotide probes comprising a conserved sequence from the endo-1,4-β-glucanase cDNA. The DNA library can be either a genomic or cDNA library. The preferred conserved sequences are:

```
5' TCCATATCTTCIGGICGTTCCCAACA 3'   and
      G  C         C     G

5' TTATCICCIGCATCATAATAICCICC 3'
      G        G  G
```

Finally, a DNA construct is provided comprising a promoter sequence operably linked to a DNA sequence encoding a signal peptide from tomato endo-1,4-β-glucanase, the DNA sequence being joined to other than a sequence encoding mature tomato endo-1,4-β-glucanase.

DESCRIPTION OF THE PREFERRED EMBODIMENT

Figure 1:
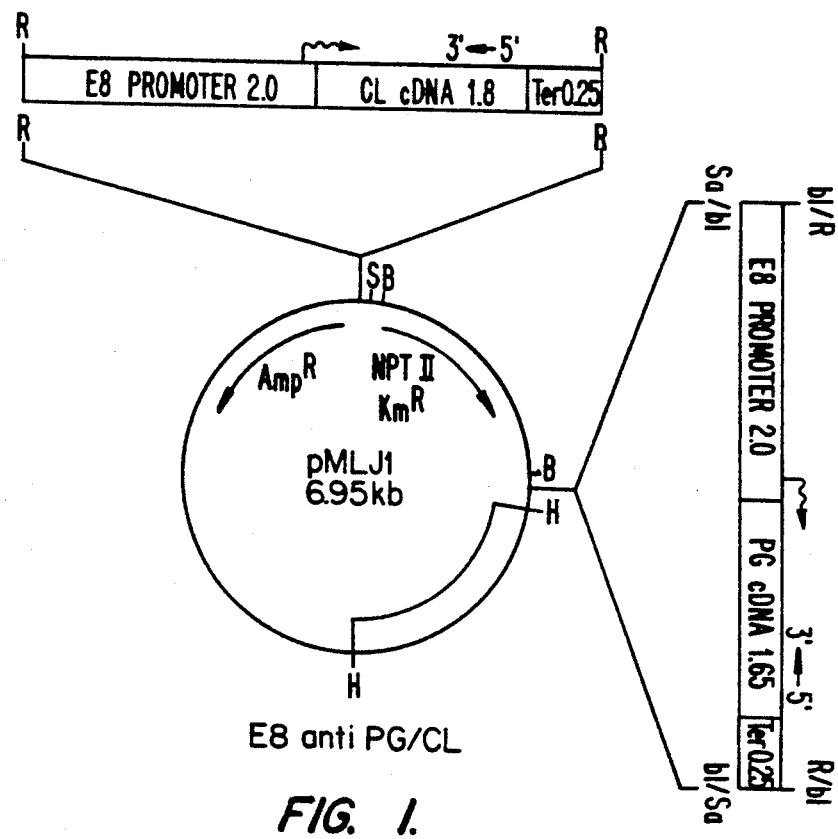
FIGS. 1-2 illustrate the construction of the pMLJ1:E8antiPG/CL and pMLJ1:CamVantiPG/CL vectors, respectively.

An improved method of reducing fruit softening in various agronomically important plant species is provided. The method comprises transforming a plant cell with an expression cassette having a plant promoter operably linked to endo-1,4-β-glucanase (glucanase) DNA in the opposite orientation for normal expression. In addition, a second expression cassette can also be introduced that comprises polygalacturonase DNA in the opposite orientation for normal expression. The glucanase cDNA can also be inserted in correct orientation for expression of the gene in plant or bacterial cells. Also provided are nucleic acid probes comprising conserved regions of the endo-1,4-β-glucanase gene which can be used to isolate the gene from any plant species. The cDNA sequence provided by this invention can be used to construct vectors capable of expressing fusion proteins comprised of the glucanase signal peptide fused to any foreign gene. This provides for the secretion of foreign gene products from the plant cell.

Control of the rate of fruit softening during the ripening process is of tremendous economic importance. In the case of tomatoes, inhibition of fruit softening allows fresh market tomatoes to remain firm while ripening on the vine. Vine ripened tomatoes have better flavor and color development then those that are picked while green. Control of fruit ripening may also improve fruit quality by increasing pathogen resistance. These properties allow for longer shelf and shipping life of the tomato fruit. Inhibition of cell wall degradation may also enhance the processing characteristics of the tomato fruit by increasing fruit viscosity.

The present invention provides a method for reducing fruit softening by inhibiting the activity of glucanase in various agronomically important species. In the exemplified case, cDNA from the tomato glucanase gene is used to create expression cassettes comprising antisense DNA to control the activity of the gene during fruit ripening.

Recombinant DNA techniques are used to introduce the antisense cDNA sequence into a suitable vector which is subsequently used to transform a suitable host cell. In the exemplified case, *Agrobacterium tumefaciens* is used as a vehicle for transmission of the cDNA to the ultimate host, the tomato cell. A plant regenerated from the transformed cell transcribes the antisense cDNA which inhibits activity of the enzyme. In plant cells, it has been shown that cDNA inhibits gene expression by preventing the accumulation of mRNA which results in decreased levels of the protein encoded by the gene, Sheehy et al., supra.

The following descriptions will detail various methods available to introduce and express foreign DNA sequences in plant cells. Specific examples of preferred methods are also described.

In summary, the manipulations necessary to prepare antisense glucanase cDNA and introduce it into a plant cell involve 1) isolating mRNA from ripe fruit, 2) preparing cDNA from the mRNA, 3) screening the cDNA for the desired sequence, 4) linking a plant promoter to the desired cDNA in the opposite orientation for expression of the glucanase gene, 5) transforming suitable host plant cells, and 6) selecting and regenerating cells which transcribe the inverted sequence.

I. General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989. The manual is hereinafter referred to as "Sambrook". Other general references are provided throughout this document. The procedures therein are believed to be well known in the art and are provided for the convenience of the reader. All the information contained therein is incorporated herein by reference.

II. Preparation of endo-1,4-β-glucanase cDNA.

To prepare glucanase cDNA, mRNA from ripe fruit is first isolated. Eukaryotic mRNA has at its 3' end a string of adenine nucleotide residues known as the poly-A tail.

Short chains of oligo d-T nucleotides are then hybridized with the poly-A tails and serve as a primer for the enzyme reverse transcriptase. This enzyme uses RNA as a template to synthesize a complementary DNA strand. A second DNA strand is then synthesized using the first cDNA strand as a template. Linkers are added to the double-stranded cDNA for insertion into a plasmid or λ phage vector for propagation in *E. coli*.

Identification of clones harboring the desired cDNA is performed by either nucleic acid hybridization or immunological detection of the encoded protein, if an expression vector is used. The bacterial colonies are then replica plated on nitrocellulose filters. The cells are lysed and probed with either oligonucleotides complimentary to the desired cDNA or with antibodies to the desired protein.

The nucleotide sequence of the cDNA encoding tomato endo-1,4-β-glucanase is provided in Table I, below. The cDNA was deposited with the American Type Culture Collection, under the provisions of the Budapest Treaty on Apr. 20, 1990, and has Accession No. 68312. The sequence may be used in any of a number of ways. Fragments of the sequence can be used as probes to identify glucanase genes in genomic or cDNA libraries prepared from other plant species.

The cDNA can be inserted in the antisense direction into expression cassettes to inhibit the expression of the glucanase gene in plant cells. The cDNA sequence, itself, can also be inserted in an expression cassette for expression in bacteria or plant cells. Insertion of the expression cassette in bacteria is useful for biomass conversion of plant tissues to ethanol or methanol.

The sequence provided can also be used for expression of fusion proteins comprised of a portion of the glucanase enzyme fused to another protein. Of particular interest is the transit peptide sequence of the protein. As is well known in the art, proteins transported across the cell membrane typically have an N-terminal sequence rich in hydrophobic amino acids about 15 to 30 amino acids long. Sometime during the process of passing through the membrane, the signal sequence is cleaved by signal peptidase. Watson et al., *Molecular Biology of the Gene,* p. 731, 1987. Thus, the signal peptide encoding sequence of the tomato endo-1,4-$\beta$-glucanase gene may be linked to another, foreign, structural gene to provide for transport of the foreign gene product to the cell wall. The foreign structural gene may be derived from any source including bacteria, yeast, animals or plants. Typically, the signal peptide encoding sequence will be joined at its 3' end to a linker for attachment to the foreign structural gene in the proper reading frame. Foreign genes of interest include carbohydrate and cell wall metabolizing enzymes, such as invertase, dextransucrase, levansucrase. Also of interest are genes that encode proteins involved in disease resistance such as chitinase, hydroxyprotein-rich glycoproteins, and polygalacturonase inhibiting proteins.

III. Vector construction

The desired recombinant vector will comprise an expression cassette designed for initiating transcription of the antisense cDNA in plants. Companion sequences, of bacterial or viral origin, are also included to allow the vector to be cloned in a bacterial or phage host.

The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

A bacterial expression vector may be used if expression of the glucanase cDNA in bacteria is desired. Insertion of an expression vector into bacteria is useful in biomass conversion of plant tissues to ethanol or methanol. Construction of a bacterial expression vector is typically done by placing the cDNA downstream from a strong bacterial promoter. Examples of bacterial promoters that might be used include $\beta$-lactamase, $\beta$-galactosidase, and the phage $\lambda$pL promoters. The efficiency of translation of mRNA in bacteria is critically dependent on the presence of a ribosome-binding site and its distance from the transcription initiation codon.

For expression in plants, the recombinant expression cassette will contain in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

```
ATAAACATAA TATTAAATAG TCATAAACCA TATGTTAAAT AATAATAATA ATTAATTAAT

AATAACAAT ATG GCT TGT TCA AAG AAT ATT TGG GTT ATT GTT ATA TTC
           Met Ala Cys Ser Lys Asn Ile Trp Val Ile Val Ile Phe
           1             5                     10
TTT TTG TGC ATT TTG GCT GGT CCT ATT ATT GCT CAA GAT TAC AAT GAT
Phe Leu Cys Ile Leu Ala Gly Pro Ile Ile Ala Gln Asp Tyr Asn Asp
     15                  20                  25
TCA CTT GGC AAA GCT ATT TTA TTC TTT GAA GGG CAA CGT TCT GGA AAA
Ser Leu Gly Lys Ala Ile Leu Phe Phe Glu Gly Gln Arg Ser Gly Lys
30                      35                  40                  45
TTA CCA GTT TCT CAA AGA GTC AAA TGG AGA GGA GAT TCC GCA CTC ATC
Leu Pro Val Ser Gln Arg Val Lys Trp Arg Gly Asp Ser Ala Leu Ile
                 50                      55                  60
GAT GGC ATA ATT GAA CAT GTG AAT TTG ATT GGA GGC TAC TAT GAT GCT
Asp Gly Ile Ile Glu His Val Asn Leu Ile Gly Gly Tyr Tyr Asp Ala
             65                      70                  75
GGT GAC AAT GTA AAA TTT GGA TGG CCC ATG GCT TAT TCT TTA ACC TTG
Gly Asp Asn Val Lys Phe Gly Trp Pro Met Ala Tyr Ser Leu Thr Leu
         80                      85                  90
TTG AGT TGG GCT GCT ATT GAA TAT CAA ACA CAA ATC TCT TCA ACA AAT
Leu Ser Trp Ala Ala Ile Glu Tyr Gln Thr Gln Ile Ser Ser Thr Asn
     95                  100                     105
CAA CTT GTA CAC CTC CAA AAT GCA ATT CGT TGG GGC ACA AAT TTC TTA
Gln Leu Val His Leu Gln Asn Ala Ile Arg Trp Gly Thr Asn Phe Leu
110                     115                     120                 125
ATT CGA GCC CAT ACT TCA AGT ACA ACT CTC TAT ACT CAG GTT GGA GAT
Ile Arg Ala His Thr Ser Ser Thr Thr Leu Tyr Thr Gln Val Gly Asp
                 130                     135                 140
GGA AAT GCA GAT CAC CAA TGT TGG GAA AGA CCA GAA GAC ATG GAT ACT
```

-continued

| Gly | Asn | Ala | Asp | His | Gln | Cys | Trp | Glu | Arg | Pro | Glu | Asp | Met | Asp | Thr |
|-----|-----|-----|-----|-----|-----|-----|-----|-----|-----|-----|-----|-----|-----|-----|-----|
|     |     |     | 145 |     |     |     |     | 150 |     |     |     |     | 155 |     |     |
| CCT | AGA | ACA | CTA | TAT | AAA | ATA | ACA | TCA | AAT | TCT | CCA | GGA | TCT | GAG | GTG |

| Pro | Arg | Thr | Leu | Tyr | Lys | Ile | Thr | Ser | Asn | Ser | Pro | Gly | Ser | Glu | Val |
|-----|-----|-----|-----|-----|-----|-----|-----|-----|-----|-----|-----|-----|-----|-----|-----|
|     |     | 160 |     |     |     |     | 165 |     |     |     |     | 170 |     |     |     |
| GCA | GCT | GAC | GTG | GCA | GCT | GCT | TTT | GCT | GCT | GCT | TCA | ATA | GTT | TTC | AAA |

| Ala | Ala | Asp | Val | Ala | Ala | Ala | Phe | Ala | Ala | Ala | Ser | Ile | Val | Phe | Lys |
|-----|-----|-----|-----|-----|-----|-----|-----|-----|-----|-----|-----|-----|-----|-----|-----|
|     |     | 175 |     |     |     |     | 180 |     |     |     |     | 185 |     |     |     |
| AAT | ATT | GAT | TCC | AAC | TAT | TCT | ACA | AAG | TTA | TTA | AAA | AGA | TCA | AGA | TCC |

| Asn | Ile | Asp | Ser | Asn | Tyr | Ser | Thr | Lys | Leu | Leu | Lys | Arg | Ser | Arg | Ser |
|-----|-----|-----|-----|-----|-----|-----|-----|-----|-----|-----|-----|-----|-----|-----|-----|
| 190 |     |     |     |     | 195 |     |     |     |     | 200 |     |     |     |     | 205 |
| TTA | TTT | GCA | TTT | GCG | GAT | AAG | TAT | AGA | GGA | TCT | TAC | CAA | GCT | TCT | TGT |

| Leu | Phe | Ala | Phe | Ala | Asp | Lys | Tyr | Arg | Gly | Ser | Tyr | Gln | Ala | Ser | Cys |
|-----|-----|-----|-----|-----|-----|-----|-----|-----|-----|-----|-----|-----|-----|-----|-----|
|     |     |     |     | 210 |     |     |     |     | 215 |     |     |     |     | 220 |     |
| CCA | TTC | TAT | TGT | TCC | TAC | TCA | GGT | TAT | AAG | GAT | GAA | TTG | TTG | TGG | GCT |

| Pro | Phe | Tyr | Cys | Ser | Tyr | Ser | Gly | Tyr | Lys | Asp | Glu | Leu | Leu | Trp | Ala |
|-----|-----|-----|-----|-----|-----|-----|-----|-----|-----|-----|-----|-----|-----|-----|-----|
|     |     |     | 225 |     |     |     |     | 230 |     |     |     |     | 235 |     |     |
| GCT | GCT | TGG | CTA | TAT | AAG | GCA | GGT | GGA | GGA | AAC | AAT | TAT | TTA | AAT | TAT |

| Ala | Ala | Trp | Leu | Tyr | Lys | Ala | Gly | Gly | Gly | Asn | Asn | Tyr | Leu | Asn | Tyr |
|-----|-----|-----|-----|-----|-----|-----|-----|-----|-----|-----|-----|-----|-----|-----|-----|
|     |     | 240 |     |     |     |     | 245 |     |     |     |     | 250 |     |     |     |
| GCT | TCA | ATC | AAC | CAA | GGT | TGG | AGT | CAA | GTT | GCC | TCT | GAG | TTT | AGT | TGG |

| Ala | Ser | Ile | Asn | Gln | Gly | Trp | Ser | Gln | Val | Ala | Ser | Glu | Phe | Ser | Trp |
|-----|-----|-----|-----|-----|-----|-----|-----|-----|-----|-----|-----|-----|-----|-----|-----|
|     | 255 |     |     |     |     | 260 |     |     |     |     | 265 |     |     |     |     |
| GAT | GAC | AAG | TTT | GCT | GGA | GCC | CAA | ACT | TTA | CTA | GCT | AAG | GAA | TAC | CTT |

| Asp | Asp | Lys | Phe | Ala | Gly | Ala | Gln | Thr | Leu | Leu | Ala | Lys | Glu | Tyr | Leu |
|-----|-----|-----|-----|-----|-----|-----|-----|-----|-----|-----|-----|-----|-----|-----|-----|
| 270 |     |     |     |     | 275 |     |     |     |     | 280 |     |     |     |     | 285 |
| AAT | GGA | AAG | AGC | AAT | TTG | GAA | AAA | TTC | AAG | AAA | GAT | GCT | GAT | TCA | TTT |

| Asn | Gly | Lys | Ser | Asn | Leu | Glu | Lys | Phe | Lys | Lys | Asp | Ala | Asp | Ser | Phe |
|-----|-----|-----|-----|-----|-----|-----|-----|-----|-----|-----|-----|-----|-----|-----|-----|
|     |     |     |     | 290 |     |     |     |     | 295 |     |     |     |     | 300 |     |
| ATT | TGT | GGA | TTA | ATG | CCA | GAA | AGT | AGC | TCT | ATA | CAA | ATT | AAG | ACA | ACC |

| Ile | Cys | Gly | Leu | Met | Pro | Glu | Ser | Ser | Ser | Ile | Gln | Ile | Lys | Thr | Thr |
|-----|-----|-----|-----|-----|-----|-----|-----|-----|-----|-----|-----|-----|-----|-----|-----|
|     |     |     | 305 |     |     |     |     | 310 |     |     |     |     | 315 |     |     |
| CCA | GGT | GGA | CTT | TTG | TAT | TAT | AGA | GAT | AGT | AGC | AAT | TTG | CAA | TAT | GTG |

| Pro | Gly | Gly | Leu | Leu | Tyr | Tyr | Arg | Asp | Ser | Ser | Asn | Leu | Gln | Tyr | Val |
|-----|-----|-----|-----|-----|-----|-----|-----|-----|-----|-----|-----|-----|-----|-----|-----|
|     |     | 320 |     |     |     |     | 325 |     |     |     |     | 330 |     |     |     |
| AAT | GGT | GCC | ACT | ATG | GTA | CTT | TTT | ATG | TAC | ACT | AAA | GTC | CTT | GAG | GCA |

| Asn | Gly | Ala | Thr | Met | Val | Leu | Phe | Met | Tyr | Thr | Lys | Val | Leu | Glu | Ala |
|-----|-----|-----|-----|-----|-----|-----|-----|-----|-----|-----|-----|-----|-----|-----|-----|
|     | 335 |     |     |     |     | 340 |     |     |     |     | 345 |     |     |     |     |
| GCT | GGA | ATA | GGA | GGA | GTT | ACA | TGT | GGA | TCT | GTT | AAT | TTT | TCC | ACA | TCC |

| Ala | Gly | Ile | Gly | Gly | Val | Thr | Cys | Gly | Ser | Val | Asn | Phe | Ser | Thr | Ser |
|-----|-----|-----|-----|-----|-----|-----|-----|-----|-----|-----|-----|-----|-----|-----|-----|
| 350 |     |     |     |     | 355 |     |     |     |     | 360 |     |     |     |     | 365 |
| AAG | ATT | AAA | GCC | TTT | GCA | AAA | TTA | CAG | GTT | GAC | TAC | ATA | CTT | GGA | AAC |

| Lys | Ile | Lys | Ala | Phe | Ala | Lys | Leu | Gln | Val | Asp | Tyr | Ile | Leu | Gly | Asn |
|-----|-----|-----|-----|-----|-----|-----|-----|-----|-----|-----|-----|-----|-----|-----|-----|
|     |     |     |     |     | 370 |     |     |     |     | 375 |     |     |     |     | 380 |
| AAT | CCA | CTC | AAA | ATG | TCA | TAC | ATG | GTG | GGA | TTT | GGC | AAC | AAA | TAT | CCA |

| Asn | Pro | Leu | Lys | Met | Ser | Tyr | Met | Val | Gly | Phe | Gly | Asn | Lys | Tyr | Pro |
|-----|-----|-----|-----|-----|-----|-----|-----|-----|-----|-----|-----|-----|-----|-----|-----|
|     |     |     | 385 |     |     |     |     | 390 |     |     |     |     | 395 |     |     |
| ACA | AAA | CTT | CAC | CAT | AGA | GCC | TCA | TCA | CTC | CCT | TCA | ATT | TAT | AAC | CAT |

| Thr | Lys | Leu | His | His | Arg | Ala | Ser | Ser | Leu | Pro | Ser | Ile | Tyr | Asn | His |
|-----|-----|-----|-----|-----|-----|-----|-----|-----|-----|-----|-----|-----|-----|-----|-----|
|     |     |     | 400 |     |     |     |     | 405 |     |     |     |     | 410 |     |     |
| CCA | ACT | AGG | GTG | GGG | TGC | AAC | GAT | GGC | TAT | AGT | TCA | TGG | TAC | AAT | TCT |

| Pro | Thr | Arg | Val | Gly | Cys | Asn | Asp | Gly | Tyr | Ser | Ser | Trp | Tyr | Asn | Ser |
|-----|-----|-----|-----|-----|-----|-----|-----|-----|-----|-----|-----|-----|-----|-----|-----|
|     | 415 |     |     |     |     | 420 |     |     |     |     | 425 |     |     |     |     |
| AAC | AAT | CCA | AAC | CCT | AAC | ACA | CAT | GTC | GGT | GCG | ATC | GTC | GGT | GGG | CCT |

| Asn | Asn | Pro | Asn | Pro | Asn | Thr | His | Val | Gly | Ala | Ile | Val | Gly | Gly | Pro |
|-----|-----|-----|-----|-----|-----|-----|-----|-----|-----|-----|-----|-----|-----|-----|-----|
| 430 |     |     |     |     | 435 |     |     |     |     | 440 |     |     |     |     | 445 |
| AAT | TCC | GGG | GAC | CAA | TTT | ATT | GAT | TCG | CGA | TCA | GAT | TAC | TCT | CAT | TCT |

| Asn | Ser | Gly | Asp | Gln | Phe | Ile | Asp | Ser | Arg | Ser | Asp | Tyr | Ser | His | Ser |
|-----|-----|-----|-----|-----|-----|-----|-----|-----|-----|-----|-----|-----|-----|-----|-----|
|     |     |     |     | 450 |     |     |     |     | 455 |     |     |     |     | 460 |     |
| GAA | CCC | ACG | ACT | TAT | ATG | AAT | GCA | GCA | TTT | ATA | GGG | TCC | GTG | GCC | GCT |

-continued

| | | | | | | | | | | | | | | |
|---|---|---|---|---|---|---|---|---|---|---|---|---|---|---|
| Glu | Pro | Thr | Thr | Tyr | Met | Asn | Ala | Ala | Phe | Ile | Gly | Ser | Val | Ala Ala |
| | | | 465 | | | | 470 | | | | | 475 | | |

TTG ATT GAT CAA ACC AAA GAA GGA GAA CAC TAT GGG GAA ATT AAT TCA

| | | | | | | | | | | | | | |
|---|---|---|---|---|---|---|---|---|---|---|---|---|---|
| Leu | Ile | Asp | Gln | Thr | Lys | Glu | Gly | Glu | His | Tyr | Gly | Glu | Ile Asn Ser |
| | | 480 | | | | | 485 | | | | | 490 | |

CAA TTT AAC AAA ACA GGT TTT ATG TAG T AGATAAATTA GTAAAGAAGT

| | | | | | | | |
|---|---|---|---|---|---|---|---|
| Gln | Phe | Asn | Lys | Thr | Gly | Phe | Met   * |
| | 495 | | | | | 500 | |

GAATGTCATG CAATTATTGA TAAATATATG TACATATAAT GAATTATCAT AAATGTATGA

AGCTATAAAT ATTACATAAT AGAAATAAAT AAATATCAAA AATGTATCTT TTTTTTTTT

TT

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221-227 (Kosage, Meredith and Hollaender, eds. 1983). Other sequences conferring tissue specificity, response to environmental signals, or maximum efficiency of transcription may also be found in the promoter region. Such sequences are often found within 400 bp of transcription initiation size, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. Herrara-Estrella et al., *Nature*, 303:209-213, 1983. Viral promoters include the 35S and 19S RNA promoters of cauliflower mosaic virus. Odell et al. *Nature*, 313:810-812, 1985. Possible plant promoters include the ribulose-1,3-bisphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J.* 7:3315-3327, 1988. which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419-434, 1982. Polyadenylation is of importance for expression of the glucanase cDNA in plant cells. Polyadenylation sequences include, but are not limited to the Agrobacterium octopine synthase signal (Gielen et al., *EMBO J.*, 3:835-846, 1984) or the nopaline synthase signal (Depicker et al., *Mol. and Appl. Genet*, 1:561-573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow an a medium containing the particular antibiotic.

IV. Transcription of endo-1,4-β-glucanase antisense cDNA in Plant Cells

A. Transformation of Plant Cells by In Vitro Techniques

1. Direct Transformation

The vector described above can be microinjected directly into plant cells by use of micropipettes to mechanically transfer the recombinant DNA. Crossway, *Mol. Gen. Genetics*, 202:179-185, 1985. The genetic material may also be transferred into the plant cell using polyethylene glycol, Krens, et al., *Nature*, 296, 72-74, 1982.

Another method of introduction of nucleic acid segments is high velocity ballistic penetration by small particles with the nucleic acid either within the matrix of small beads or particles, or on the surface, Klein, et al., *Nature*, 327, 70-73, 1987.

Yet another method of introduction is fusion of protoplasts with other entities, either minicells, cells, lysosomes or other fusible lipid-surfaced bodies, Fraley, et al., *Proc. Natl. Acad. Sci. USA*. 79, 1859-1863, 1982.

The DNA may also be introduced into the plant cells by electroporation. Fromm et al., *Pro. Natl Acad. Sci. USA*, 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

2. Vectored Transformation

Cauliflower mosaic virus (CaMV) may be used as a vector for introducing the antisense DNA into plant cells. (Hohn et al., 1982 *"Molecular Biology of Plant Tumors."* Academic Press, New York, pp. 549-560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

Another method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237: 1176-1183, 1987.

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid. Hoekema, et al., *Nature*, 303:179-189, 1983. The transferred DNA region can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, 1981, Nature 298:85-88), promoters, Lawton et al., 1987, Plant Mol. Biol. 9:315-324) and structural genes for antibiotic resistance as a selection factor (Fraley et al., *Proc. Nat. Acad. Sci.*, 80:4803-4807, 1983).

All plant cells which can be transformed by Agrobacterium and from which whole plants can be regenerated can be transformed according to the present invention to produce transformed intact plants which contain the desired DNA. There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for culturing protoplasts and subsequent plant regeneration from cultured protoplasts.

Method (2) requires (a) that the intact plant tissues, such as cotyledons, can be transformed by Agrobacterium and (b) that the transformed cells or tissues can be induced to regenerate into whole plants.

Most dicot species can be transformed by Agrobacterium. All species which are a natural plant host for Agrobacterium are transformable in vitro. Monocotyledonous plants, and in particular, cereals, are not natural hosts to Agrobacterium. Attempts to transform them using Agrobacterium have been unsuccessful until recently. Hooykas-Van Slogteren et al., *Nature*, 311:763-764, 1984. There is growing evidence now that certain monocots can be transformed by Agrobacterium. Using novel experimental approaches cereal species such as rye (de la Pena et al., *Nature* 325:274-276, 1987), corn (Rhodes et al., *Science* 240:204-207, 1988), and rice (Shimamoto et al., *Nature* 338:274-276, 1989) may now be transformed.

B. Selection and Regeneration of Transformed Plant Cells

After transformation, transformed plant cells or plants comprising the antisense DNA must be identified. A selectable marker, such as those discussed, supra, is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well. See, e.g., Sambrook, supra.

After determination of the presence of the antisense DNA, whole plant regeneration is desired. All plants from which protoplasts can be isolated and cultured to give whole regenerated plants can be transformed by the present invention. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, and Datura.

Plant regeneration from cultured protoplasts is described in Evans et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. III, 1986.

It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

V. Definitions

The phrase "DNA sequence" refers to a single or double-stranded polymer of deoxyribonucleotide bases read from the 5′ to the 3′ end. It includes both self-replicating plasmids, infectious polymers of DNA and non-functional DNA.

The term "promoter" refers to a region of DNA upstream from the structural gene and involved in recognition and binding RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells.

The phrase "suitable host" refers to a microorganism or cell that is compatible with a recombinant plasmid, DNA sequence or recombinant expression cassette and will permit the plasmid to replicate, to be incorporated into its genome, or to be expressed.

The term "expression" refers to the transcription and translation of a structural gene so that a protein is synthesized.

A "constitutive" promoter is a promoter which is active under all environmental conditions and all states of development or cell differentiation.

An "inducible" promoter is a promoter which is under environmental or developmental control. Examples of environmental conditions that may effect transcription by inducible promoters include anaerobic conditions or the presence of light. Examples of promoters under developmental control include promoters that initiate transcription only in certain tissues, such as the promoter from the E8 gene which is induced by ethylene in ripening fruit.

The term "opposite orientation for expression" refers to a double-stranded DNA sequence from a structural gene that is inserted in an expression cassette in an inverted manner with respect to its naturally occurring orientation. Specifically, the strand that is normally the "template strand becomes the coding strand, and vice versa.

The term "uninterrupted" refers to a DNA sequence containing an open reading frame that lacks intervening, untranslated sequences.

The term "non-wild type DNA" refers to DNA sequences that do not flank a given DNA sequence in its naturally occurring environment.

The following experimental results are offered by way of example and not by way of limitation.

EXAMPLES

A. Preparation of Tomato endo-1,4-$\beta$-glucanase cDNA

1. cDNA Library Production

A vector-primed cDNA library was prepared using standard methods. The library was prepared in the cloning vector pARC7 from ripe tomato fruit poly-A RNA by the method of Alexander et al., *Gene*, 31:79–89, 1984, which is incorporated herein by reference.

2. cDNA Library Screening a. Growing Colonies

HB101 cells containing a red ripe tomato-derived cDNA library were titered and dilutions were made to give approximately 5000 colonies per 10 ml of Luria Broth (LB). Ten ml aliquots of chilled bacterial suspension were vacuum filtered onto ten 132 mm nitrocellulose filters, which were then placed colony sides up on LB-agar plates containing 100 μg/ml ampicillin. Plates were incubated at 37° C. until colonies were approximately 0.5 mm in diameter.

b. Replica Plating

Master filters were removed from plates, numbered and given orientation marks with black ink. A fresh filter was wetted on a fresh LB plate and was laid on top of each master filter and orientation marks copied to the replicate. This process of colony transfer was repeated with a 2nd fresh filter to give two replica filters per master filter. Replicates were grown on LB-agar plates at 37° C. until colonies were approximately 0.5 mm and then were transferred to plates containing LB-agar with 150 μg/ml chloramphenicol. These were grown 12 hours at 37° C.

c. Bacterial Colony Lysis

Replica filters were removed from plates and placed colony sides up at room temperature on sheets of Whatman 3MM paper wetted with 0.5M NaOH/1.5M NaCl. After 10 minutes, filters were blotted on dry 3MM paper and transferred for 2 minutes to 3MM paper wetted with 1M Tris pH 7/1.5M NaCl. Filters were immersed in 3×SSC for 15 seconds, placed on dry 3MM paper and air dried prior to baking at 80° C. under vacuum for 2 hours.

d. Hybridization to Oligonucleotide Probe

Bacterial debris was removed from baked filters by washing with 3×SSC/0.1% SDS at 62° C. for 24 hours, during which time wash solution was replaced with fresh solution 3 times. Filters were collectively prehybridized at 37° C. overnight with 6×SSC, 1×Denhardts Solution, 0.5% SDS, 0.05% NaPPi and 0.1 mg/ml boiled and ice-quenched salmon sperm DNA. The 20 filters were then divided into two groups of replicates for hybridization.

Two 26 base oligonucleotide probe were synthesized at a DNA synthesizing facility. Probe sequences corresponded to two regions of glucanase that are completely conserved at the amino acid level in bean abscission zone glucanase and avocado fruit glucanase. Oligonucleotides were solubilized in 10 mM Tris-EDTA (TE) pH 8 and extracted with TE-saturated butanol; they were then adjusted to 0.3M in ammonium acetate and were precipitated with 4 volumes of ethanol at −80° C. DNA was harvested by centrifugation and was brought to 1 mg/ml in TE pH 8.

One μg of each oligonucleotide probe was end labeled with 32P-ATP according to the T4 DNA Polymerase Labeling System (Bethesda Research Labs) protocol supplied by the manufacturer. Specific activity of each probe exceeded $5 \times 10^7$ cpm/μg.

Each set of replica filters was incubated overnight at 42° C. in a hybridization bag containing 15 ml of hybridization buffer and one of the boiled and ice-quenched radiolabeled probes. Hybridization medium was 6×SSC, 1×Denhardt's solution, 0.05% NaPPi and 0.1 mg/ml boiled and ice-quenched salmon sperm DNA.

Filters were washed at 42° C. in 6×SSC, 0.05% NaPPi for several hours with several buffer changes. They were then exposed to Kodak X-O-Mat AR film at −80° C. for 24 hours using an intensifying screen. Film was developed and clones containing glucanase probe sequence were identified via the comparison of orientation marks on the film with those on the corresponding master plate.

e. Secondary Screening of Putative Glucanase Clones

Colonies identified by the glucanase oligonucleotide probes were picked with sterile toothpicks, dispersed into 1 ml LB and incubated with shaking at 37° C. for 2.5 hours. Suspensions were then diluted 500,000-fold and vacuum filtered in 5 ml aliquots of chilled LB through 82 mm nitrocellulose filters. These were grown at 37° C. on LB agar with 100 μg/ml ampicillin for 8 hours prior to their transfer to LB agar plates containing 150 μg/ml chloramphenicol. These were then incubated at 37° C. for 12 hours. Filters were processed and screened with radiolabeled oligonucleotides probes as per steps 3 and 4 above. Single colonies of each of the 28 glucanase clones identified in the secondary screen were picked into 3 ml of LB ampicillin and grown overnight at 37° C.

f. Southern Analysis of Glucanase Clones

Mini prep DNA was isolated from bacterial cultures by the method of Kraft et al. Biotechnicues 6(6):544–546 which is incorporated herein by reference. DNA was then digested with Sma I restriction enzyme for 2.5 hours under standard conditions to release the cloned glucanase inserts from their respective pArc vectors; digestion products were size fractionated on 1.2% agarose gels using avocado glucanase cDNA and tomato polygalacturonase cDNA clones as positive and negative controls, respectively. Following incubation in 250 mM HCl, followed by 0.5M NaOH/1.5M NaCl and finally by 0.5M Tris/3M NaCl, gels were blotted to nitrocellulose and probed with each oligonucleotide probe end labeled as previously described. The largest glucanase insert was estimated to be 1.8 kilobases, similar to the previously characterized 1.9 kB avocado glucanase cDNA. This clone was selected for sequencing.

3. Sequencing of Tomato Glucanase a. Subcloning of Tomato Glucanase

Sma I digestion of mini prep DNA prepared from the colony described in step 6 of part 1 released the 1.8 kB (estimated size) glucanase clone from the pArc vector. Digestion products were precipitated with 0.4 volumes ammonium acetate and 2 volumes ethanol and resuspended in 1×DNA sample buffer. Products were loaded onto a low-melt agarose gel with insert separated from vector by electrophoresis at 80 V. The insert was excised from the gel and stored as a gel slice at −20° C. until required. DNA concentration was estimated from the relative intensities of ethidium bromide staining between insert and defined standards.

Bluescript vector (SK+) (Stratagene Inc., La Jolla, Calif.) was linearized by Sma I digestion under standard conditions at 30° C. After 2.5 hours, digested vector was extracted once with phenol:chloroform:isoamyl alcohol (25:24:1) and once with chloroform-isoamyl alcohol (24:1) prior to precipitation with 0.4 volumes ammonium acetate and 2.5 volumes ethanol. The pelleted DNA was brought up in 500 μl 50 mM Tris, 0.1 mM EDTA, pH 8 and was dephosphorylated with Boehringer Mannheim calf intestine alkaline phosphatase as per the manufacturer's instructions for blunt ended DNA fragments. Dephosphorylated vector was harvested by ammonium acetate/EtOH precipitation as described previously and was brought to 100 μg/ml with water.

Dephosphorylated vector was ligated at 15° C. for 12 hours to melted glucanase insert from the low melt agarose gel. Ligation specifications were as follows for each 45 μl ligation: total DNA concentration=1 μg, insert:vector=2.1 on a molar basis. T4 DNA ligase=100 units/ml, final PEG concentration=5%.

Ligation mixtures were brought up to 100 μl with TE 8.0 and added to 200 μl freshly thawed XL1 Blue competent cells. After 30 minutes on ice, cells were heat shocked 5 minutes at 42° C. and added to 4 ml 2XL medium which had been prewarmed to 37° C. Cells were shaken at 100 rpm on an orbital shaker for 100 minutes at 37° C. and transferred to ice. Appropriate aliquots of the cells were then spread on LB agar plates containing 100 μg/ml ampicillin and 50 μg/ml tetracycline. Plates had been pre-spread with 100 μl of (50 μl 100 mM IPTG, 20 μl 20 mg/ml X-gal, 30 μl LB). Plates were then incubated overnight at 37° C., at which time transformed colonies (white) could be distinguished from non-transformed colonies (blue). Miniprep DNA was isolated from transformants as previously described and digested with Sma I to release inserts. One glucanase transformant of approximately 1.8 kB was identified following the electrophoretic separation of digestion products on a 1.5% agarose gel. Double stranded miniprep DNA was prepared as previously described for sequencing purposes.

b. Sequencing

Double stranded DNA templates of varying lengths for use in first strand sequencing were generated by exonuclease digestion of glucanase miniprep DNA as described in the Erase-A-Base kit (Promega) protocol supplied by the manufacturer. Sequencing was conducted by the dideoxy method (Sanger, et al., *Proc. Nat. Acad. Sci. USA*, 74:5463–5467) outlined fully in the Sequenase kit (United States Biochemical Co.) protocol provided by the manufacturer. Reverse M13 primer was purchased from Pharmacia.

Sequence data generated was entered and analyzed using the Microgenie sequence analysis computer program (Beckman Instruments, Inc.) strand resulted from the overlap of over 20 smaller sequences.

B. Vector Construction

Figure 2:
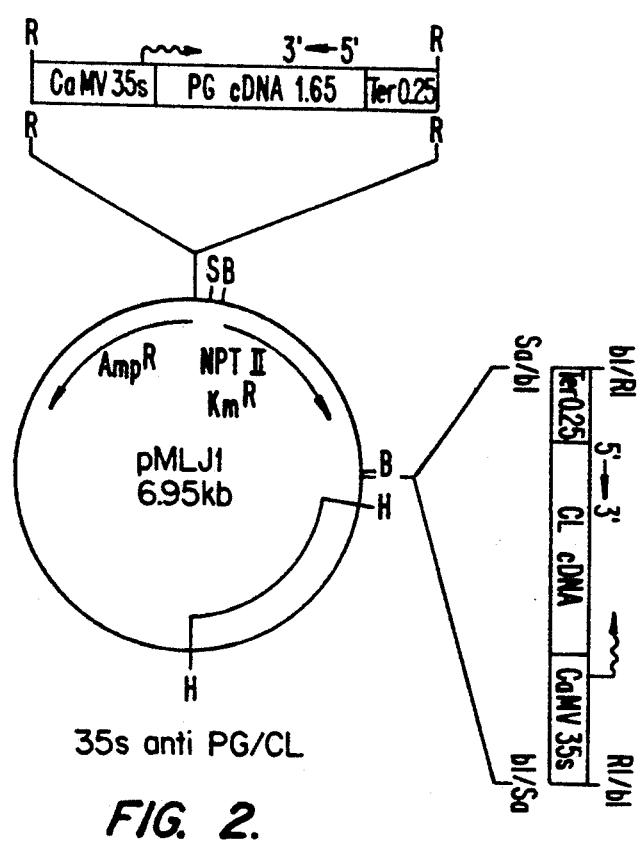

Four different vectors were constructed. One vector, E8antiCL, contains the promoter from the tomato E8 gene and glucanase antisense DNA. This promoter is inducible in ripening tomato fruit. The second vector, CaMVantiCL, contains the cauliflower mosaic virus 35S promoter and glucanase antisense DNA. This promoter is constitutive. The other two vectors were constructed in the same manner but with the addition of polygalacturonase antisense DNA and appropriate promoters. The construction of the latter two vectors is illustrated in FIG. 2

1. E8antiCL

A 2.0 kb E8 promoter fragment was isolated by cleaving pE8mutRN2.0 with NcoI. The preparation of pE8mutRN2.0 is described in Giovaninnoni et al., *The Plant Cell*, 1:53–63, 1989, which is incorporated herein by reference. The 5' overhang of the NcoI restriction site was blunt-ended with the large fragment of DNA polymerase (Klenow fragment) and digested with EcoR1 restriction endonuclease. The resulting 2.0 kb EcoR1/filled NcoI fragment was ligated into pUC118 cleaved with EcoR1 and Sma1 restriction endonucleases. The resulting construction, pE8mutRN2.0(+), retains the original NcoI restriction site and includes BamH1, XbaI, Sal1, Pst1, Sph1, and HindIII sites downstream of the NcoI restriction site.

The 1.8 kb endo-1,4-$\beta$-glucanase cDNA cloned into the Sma1 site of the Bluescript M13+ (SK+) vector (Stratagene Inc., La Jolla, Calif.) was liberated by digestion with BamH1 and Kpn1 followed by agarose gel purification. The fragment was then ligated into BamH1/Kpn1 digested pUC118 to generate pUCCL1.8. The 1.8 kb BamH1/Sst1 cDNA insert of PUCCL1.8 was liberated by restriction endonuclease digestion and purified by agarose gel electrophoresis.

The resulting 1.8 kb BamH1/Sst1 fragment was utilized in a tri-molecular ligation with the 0.25 kb Sst1/EcoR1 Agrobacterium nopaline synthase gene transcription terminator fragment (capable of directing termination of gene transcription in plants) purified from pBI121 (Clonetech Inc., Palo Alto, Calif.) and ligated into pUC118 cleaved with BamHI and EcoRI. The resulting pUCantiCL-ter construction contained the glucanase cDNA fused at its 5' end to the nopaline synthase gene transcription termination fragment via Sst1 site ligation. The 2.05 kb antiCL-ter fragment was isolated from pUCantiCL-ter by digestion with BamH1 followed by partial digestion with EcoR1. The 2.05 kb product was then purified on a agarose gel.

The resulting 2.05 kb EcoR1/BamH1 fragment was utilized in a tri-molecular ligation with the 2.0 kb EcoR1/BamH1 fragment purified from pE8mutRN2.0 and pUC118 cleaved with EcoR1. The resulting construction, pE8antiCL, contains the E8 promoter fused to the 3' end of the glucanase cDNA clone with the 5' end fused to the transcription termination fragment of the nopaline synthase gene. The internal EcoR1 site located between the cDNA and transcription terminator sequences was removed by partial digestion with EcoR1 restriction endonuclease followed by filling in of the EcoR1 5' overhang with Klenow enzyme and subsequent ligation of the filled in EcoR1 restriction endonuclease sites. The loss of the internal EcoR1 site was verified by restriction endonuclease mapping of the resulting construction, pE8antiCL-R1. The 4.05 kb insert of pE8antiCL-R1 was liberated with EcoR1 restriction endonuclease, purified by agarose gel electrophoresis, and ligated into the EcoR1 site of the Agrobacterium T-DNA cointegrative shuttle vector pMLJ1, described in subsection 3, infra. The resulting construction is designated pMLJ1:E8antiCL.

2. CaMVantiCL

Regulatory sequences of the Cauliflower Mosaic Virus 35s transcription unit Were isolated from pBI121 (Clonetech Inc., La Jolla, Calif.) by digestion with SphI and BamHI followed by agarose gel purification. The resulting 0.8 kb SphI/BamHI fragment was employed in a tri-molecular ligation with the 2.05 kb BamHI/EcoRI fragment of pUCantiCL-ter (described above) and pUC118 digested with Sph1 and EcoR1. The resulting construction was partially digested with EcoR1, and subjected to a fill-in reaction with Klenow enzyme followed by ligation to remove the internal EcoR1 restriction endonuclease site located between the 5' end of the cDNA and the plant transcription termination sequences. Restriction endonuclease mapping was employed to verify that the EcoR1 site between the cDNA and transcription termination sequences was removed. The resulting construction was designated pCaMVantiCL-S. pCaMVantiCL-S was digested with Sph1. The 3' overhang resulting from Sph1 digestion was filled in using T4 DNA polymerase and ligated to EcoRI linkers (BRL, Bethesda, Md.). The resulting construction was termed pCaMVantiCL. The 2.85 kb insert of pCaMVantiCL was isolated via digestion with EcoR1 restriction endonuclease followed by agarose gel purification and ligated into the EcoRI site of pMLJ1 to generate pMLJ1:CaMVantiCL.

3. E8antiPG/CL

The 1.7 kb full length tomato fruit polygalacturonase cDNA insert of pBSPG1.9 (DellaPenna et al., *Plant Physiology* 90:1372–1377, 1989 which is incorporated herein by reference), cloned into the Sma1 site of the Bluescript M13+ (SK+) vector was liberated by digestion with Sal1 and Sst1 restriction endonucleases followed by agarose gel purification. The resulting 1.7 kb fragment was utilized in a tri-molecular ligation with the 0.25 kb Sst1/EcoR1 Agrobacterium nopaline synthase gene transcription termination sequence (described above) and Sal1/EcoR1 digested pUC118. The resulting construction was designated pUCantiPG-ter and consists of the 5' end of the polygalacturonase cDNA clone fused to the nopaline synthase transcription termination sequence at the Sst1 site.

The 1.95 kb insert of pUCantiPG-ter was liberated by digestion with Sal1 and EcoR1 restriction endonucleases followed by agarose gel purification. The resulting 1.95 kb Sal1/EcoR1 fragment was utilized in a tri-molecular ligation with the 2.0 kb EcoR1/Sal1 E8 promoter fragment isolated from pE8mutRN2.0(+) (described above) and pUCE8antiPG.

The 3.95 kb insert of pUCE8antiPG was isolated by agarose gel purification following digestion with EcoR1 restriction endonuclease and subsequent DNA polymerase (Klenow) fill-in of the 5' EcoR1 overhangs bordering both sides of the 3.95 kb antisense gene. The unique SalI restriction site of the cointegrative plant transformation vector, pMLJ1, was cleaved with SalI and filled in with Klenow enzyme. The blunt ended 3.95 kb E8antiPG fragment was ligated into the blunt ended SalI site of pMLJ1 to form pMLJ1:E8antiPG. pMLJ1:E8antiPG was cleaved in the unique EcoR1 site of the pMLJ1 sequences. The 4.05 kb insert of pE8antiCL-R1 (described above) was liberated with EcoR1 and purified by agarose gel electrophoresis. The resulting 4.05 kb E8antiCL-R1 fragment was ligated into the EcoR1 site of pMLJ1:E8antiPG to form pMLJ1:E8antiPG/CL (see FIG. 2).

4. CaMVantiPG/CL

Regulatory sequences of the Cauliflower Mosaic Virus 35S transcription unit were isolated from pBI121 as described above. The 1.95 kb insert of pUCantiPG-ter (described above) was isolated by digestion with EcoRI and partial digestion with BamHI, followed by agarose gel purification of the resulting 1.95 kb fragment. The resulting 0.8 kb Sph1/BamH1 fragment of the CaMV 35S promoter was employed in a tri-molecular ligation with the 1.95 kb BamHI/EcoR1 insert of pUCantiPG-ter and pUCl18 digested with Sph1 and EcoR1 restriction endonucleases to produce the construction designated pUCCaMVantiPG-S co. pUCCaMVantiPG-S was digested with Sph1. The 3' overhang resulting from Sph1 digestion was filled in using T4 DNA polymerase and ligated to EcoRI linkers (BRL, Bethesda, Md.). The resulting construction was termed pUCCaMVantiPG and contains the 2.75 kb CaMVantiPG gene cloned into the EcoR1 site of pUC118.

The 2.85 kb insert of pCaMVantiCL was isolated by agarose gel electrophoresis following digestion with EcoR1 restriction endonuclease and filling in of the 5' EcoR1 overhangs with Klenow enzyme. The unique SalI site of pMLJ1 was cleaved with SalI and filled in with Klenow enzyme. The 2.85 kb blunt end CaMVantiCL fragment was ligated into the EcoR1 site of pMLJ1:CaMVantiCL2 to form pMLJ1:CaMVantiPG/CL (see FIG. 2).

5. Co-integration of Antisense Gene Constructions

Triparental mating was done according to methods well known in the art as described in Van Haute et al., *EMBO J.* 411–417, 1983, which is incorporated herein by reference. The shuttle vector used in the triparental mating is not a critical aspect of the invention. The particular shuttle vector used here, pMLJ1, is derived from that described in DeBloch et al., *EMBO J.* 3:1681–1689, 1984.

Triparental mating of *E. coli* (strain JM109) harboring pMLJ1:E8antiCL, pMLJ1:CaMVantiCL, pMLJ1:E8antiPG/CL, or pMLJ1:CamVantiPG/CL with *Agrobacterium tumefaciens* containing the cointegrative plant transformation vector pGV3850 (this vector is described in detail in Zambryski et al., *EMBO J.* 2:2143, 1983, which is incorporated herein by reference) and the helper *E. coli* strain pGJ23 resulted in cointegration of the antisense gene constructions into pGV3850, pGV3850:E8antiCL and pGV3850:CaMVantiCL were utilized to insert antisense endo-1,4-β-glucanase sequences into the tomato genome.

C. Transformation of Tomato With Antisense Endo-1,4-β-Glucanase Constructions

Summary of the Procedure

In brief, sterile cotyledon pieces were infected with Agrobacterium containing a Ti plasmid which includes within the T-DNA a neomycin phosphotransferase gene (NPT11) capable of conferring kanamycin resistance in transgenic plants. The co-integrative *Agrobacterium tumefaciens* Ti vector, pGV3850, with pMLJ1:E8antiCL, pMLJ1:CaMVantiCL, pMLJ1:E8antiPG/CL or pMLJ1:CamVantiPG/CL independently integrated into it, was used to transfer the two antisense gene constructions into independent tomato genomes. Co-cultivation of tomato (*Lycopersicon esculentum* cv Ailsa Craig) cotyledon pieces with the bacteria took place for 48 hours on tobacco feeder plates. The feeder cells increase the efficiency of transformation of tomato after the co-cultivation process. Regeneration of shoots was induced on the regeneration medium. From this stage on, antibiotics were used to inhibit the growth of Agrobacterium (Cefotaxime) and to select for transformed plant cells (kanamycin). Finally, shoots were transferred to rooting medium and then planted in soil and grown in the greenhouse.

1. Maintenance of Feeder Cells

To maintain the tobacco Xanthi suspension culture the cells were filtered through a 40 mesh filter once per week. 10 mls of filtrate were added to 100 mls of fresh Xanthi medium in a 500 ml flask.

2. Tomato Seed Germination

Approximately 50 seeds in a 50 ml beaker were stirred in 20 mls 70% EtOH for 2 minutes and rinsed with sterile water. They were then stirred 5 minutes in 20% bleach with 2 drops of Tween 80 and rinsed 4 times with sterile distilled $H_2O$.

Using sterile forceps, 12 to 15 seeds were placed on each plate. The petri plate was wrapper with parafilm and aluminum foil and grown at 25° C. After 5 days (when the seeds had reached about 60% germination), they were removed from the aluminum foil and grown under 2500 lux, with a 16 hour photoperiod. The seedlings were grown for a total of 8 days.

3. Preparation of Feeder Plates

Thick petri plates of approximately 40 mls of Xanthi suspension culture medium with 8 g/l agar were employed. 1 ml of a thick Xanthi suspension culture (7 days old) was pipetted onto each feeder plate. The plates were sealed with parafilm and incubated for 12 hours in the growth chamber (25° C.) on a lighted shelf.

4. Putting Cotyledons on the Feeder Plates

A sterile Whatman #1 filter was placed onto each feeder cell plate. Cotyledons were cut with a scalpel in a drop of sterile water in a petri plate. The scalpel was rocked gently to make the cuts thus minimizing tearing and bruising of the tissue. Only the ends of the cotyledons were cut off. Cut cotyledons were placed onto the filter paper on the feeder plate upside-down (cuticle side down). Approximately 50 cotyledon pieces were placed on each plate. The plates were sealed with parafilm and placed in the growth chamber for 16 hours.

5. Infection with Transformed Agrobacterium 10 ml overnight cultures of the Agrobacterium containing pMLJ1:E8antiCL and pMLJ1:CaMVantiCL were grown in YE8 medium supplemented with 25 µg/ml spectinomycin. Agrobacterium overnight cultures were diluted four-fold in the seed germination medium to an O.D. of 590. 0.5 mls of diluted bacteria were aliquoted into a petri dish followed by addition 30 cotyledon pieces previously co-cultivated with tobacco feeder cells. The Agrobacterium/cotyledon mixture was swirled to wet. The cotyledons were wet in the bacteria for 5 minutes. The cotyledons were touched once to a sterile paper towel. Cotyledons were placed back on the same feeder plates upside-down and co-cultivated for an additional 48 hours.

6. Regeneration

After co-cultivation with the bacteria, cotyledons were placed on the regeneration medium right-side-up. The edges of the cotyledon will curl down into the agar insuring the wounded surfaces will be in direct contact with the drugs. 15 cotyledon pieces were placed on each plate.

Within 10 days callus was visible at the edges of the infected cotyledons. Cotyledon pieces were transferred to fresh plates every 2 weeks. Shoots and dark green callus was transferred to shooting medium (same as regeneration medium except that the zeatin concentration is reduced to 0.1 mg/ml). After 6 weeks (3 transfers) all callus and shoots were transferred to shooting medium.

For rooting, TM5 rooting medium was employed. (Shahin, Theor. Appl. Gen. 69: 235–240, 1985). The levels of kanamycin and cefatoxime are reduced to 25 mg/l and 125 mg/l, respectively.

After the shoots developed sufficient roots, they were transferred to soil. To transfer plants to soil, they were gently removed from the agar using a spatula to scrape away most of the agar. The roots were rinsed in warm water to remove as much agar as possible. They were planted in clay pots which were placed inside GA-7 boxes. The covers of the boxes were gradually opened over several days and watered with ½-strength Hoagland's solution every other watering. After 2 weeks, the plants were completely uncovered in the growth chamber and were transplanted into large pots and moved to the greenhouse.

7. Media a. Xanthi Suspension Culture Medium

|  | stock |  |
|---|---|---|
| 1 bottle KC MS Salts (MM100) | 4.3 g |  |
| i-inositol | 100 mg |  |
| sucrose | 30 g |  |
| $KH_2PO_4$ | 2 mls | 100 mg/ml |
| thiamine | 1.3 mls | 1 mg/ml |
| 2,4-D | 2 mls | 100 mg/l |
| kinetin | 0.4 mls | 0.25 mg/ml |
| pH 5.5 with KOH |  |  |
| $H_2O$ to 1 liter |  |  |
| aliquot 100 mls into 500 ml flasks |  |  |
| plug the flasks and cap with aluminum foil |  |  |
| autoclave 20' |  |  | b. Plates for seed germination

| MS Medium | 1 pkg. KC MM-100 |
|---|---|
| 3% sucrose | 30 g sucrose |
|  | 800 mls $H_2O$ | pH to 5.7 with KOH
volume to 1 liter
add 8 g bacto agar (0.8% agar)
autoclaved 20 minutes
poured into thick petri plates (about 30 mls per plate)

c. Regeneration medium for 1 liter:
4.3 g MS Salts (KC MM-100)
30 g glucose
0.59 g MES
2 ml 500X Gamborgs vitamins (see below)
ph to 5.8 with 1N KOH
volume to 1 liter
8 g tissue culture grade agar
Autoclave 20 minutes
Cool to 50 degrees C.
Add:

1 mg sterile zeatin (trans-isomer)
300 mg/l cefotaxime (Calbiochem Cat #219380)
50 mg/l kanamycin 500X Gamborgs vitamins:

5 g myo-inositol
0.5 g thiamine HCL
50 mg nicotinic acid
50 mg pyridoxine HCl
100 ml sterile water Cefotaxime is light sensitive. It turns yellow when it's been in the light for too long. So plates containing Cefotaxime were made the day before use.

d. TM5 for root induction

| Ingredient | amount/liter |
|---|---|
| MS salts | 4.3 g |
| Potato vitamins (200X) | 5 mls |
| Sucrose | 30 g |
| IBS (indole-3-butyric acid, Sigma) | 0.1 mg (add before autoclaving) |
| Purified agar | 7 g | adjust pH to 5.8 with KOH
Autoclave 15 minutes.
When cooled to 50° C. add 25 mg kanamycin and 125 mg cefotaxime.

Potato vitamins (200X)

| Ingredient | amount/liter |
|---|---|
| myo-inositol | 20 g |
| thiamine-HCl | 100 mg |
| pyridoxine-HCl | 100 mg |
| nicotinic acid | 1 g |
| glycine | 500 mg |
| biotin | 10 mg |
| folic acid | 100 mg | adjust pH to 5.8 to 6.0 to clear solution.
Store at −20° C.

What is claimed is:

1. A DNA construct comprising a promotor sequence operably linked to a DNA sequence encoding a signal peptide from tomato endo-1,4-β-glucanase, the DNA sequence being joined to a DNA sequence other than a sequence encoding mature tomato endo-1,4-β-glucanase.

2. A plant cell comprising a DNA construct according to claim 1.

* * * * *